United States Patent
Lee et al.

(10) Patent No.: US 10,863,926 B2
(45) Date of Patent: Dec. 15, 2020

(54) FALL DETECTION DEVICE AND METHOD FOR CONTROLLING THEREOF

(71) Applicant: SAMSUNG ELECTRONICS CO., LTD., Suwon-si (KR)

(72) Inventors: Han-sung Lee, Seoul (KR); Jae-geol Cho, Yongin-si (KR); Moo-rim Kim, Suwon-si (KR); Chang-hyun Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 281 days.

(21) Appl. No.: 15/763,160

(22) PCT Filed: Sep. 12, 2016

(86) PCT No.: PCT/KR2016/010241
§ 371 (c)(1),
(2) Date: Mar. 26, 2018

(87) PCT Pub. No.: WO2017/052126
PCT Pub. Date: Mar. 30, 2017

(65) Prior Publication Data
US 2018/0263534 A1    Sep. 20, 2018

(30) Foreign Application Priority Data

Sep. 25, 2015   (KR) .................. 10-2015-0137010

(51) Int. Cl.
*A61B 5/11*     (2006.01)
*G08B 21/04*    (2006.01)
(Continued)

(52) U.S. Cl.
CPC .......... *A61B 5/1117* (2013.01); *A61B 5/0022* (2013.01); *A61B 5/11* (2013.01);
(Continued)

(58) Field of Classification Search
CPC ... A61B 5/1117; A61B 5/0022; A61B 5/6803; A61B 5/688; A61B 5/746; A61B 5/0245;
(Continued)

(56) References Cited

U.S. PATENT DOCUMENTS

| 8,408,041 B2 | 4/2013 | Ten Kate et al. |
| 2008/0133277 A1 | 6/2008 | Jang et al. |

(Continued)

FOREIGN PATENT DOCUMENTS

| KR | 10-2010-0000317 A | 1/2010 |
| KR | 10-2013-0107144 A | 10/2013 |

(Continued)

OTHER PUBLICATIONS

Communication dated Dec. 16, 2016 by the International Searching Authority in International Patent Application No. PCT/KR2016/010241. (PCT/ISA/210).

*Primary Examiner* — Robert R Raevis
(74) *Attorney, Agent, or Firm* — Sughrue Mion, PLLC

(57) ABSTRACT

The present invention relates to a fall detection device, which includes a sensor attached to a user and sensing a motion of the fall detection device in a plurality of coordinate axial directions; an output section capable of outputting fall information of a user; and a controller determining that the user falls down when acceleration in a first axial direction among the plurality of coordinate axial directions is changed from a positive value to a negative value based on the motion sensed by the sensor, and controlling the fall information to be output.

12 Claims, 15 Drawing Sheets

(51) Int. Cl.
    *A61B 5/00*          (2006.01)
    *G01P 15/08*        (2006.01)
    *A61B 5/0402*      (2006.01)
    *A61B 5/0245*      (2006.01)
    *G01P 15/18*        (2013.01)

(52) U.S. Cl.
    CPC ............ *A61B 5/6803* (2013.01); *A61B 5/688* (2013.01); *A61B 5/746* (2013.01); *G01P 15/0802* (2013.01); *G08B 21/043* (2013.01); *G08B 21/0446* (2013.01); *A61B 5/0245* (2013.01); *A61B 5/0402* (2013.01); *A61B 2562/0219* (2013.01); *G01P 15/18* (2013.01)

(58) Field of Classification Search
    CPC ......... A61B 2562/0219; G01P 15/0802; G01P 15/18
    USPC ......... 73/514.35, 514.01–514.38; 702/33, 41
    See application file for complete search history.

(56) References Cited

U.S. PATENT DOCUMENTS

2009/0315719 A1*  12/2009  Song ................. G08B 21/0446
                                                    340/573.1
2010/0121226 A1    5/2010  Ten Kate et al.
2013/0197856 A1*   8/2013  Barfield ................. G01P 15/00
                                                    702/141

FOREIGN PATENT DOCUMENTS

KR    10-2014-0100076 A    8/2014
KR    10-2015-0068597 A    6/2015

* cited by examiner

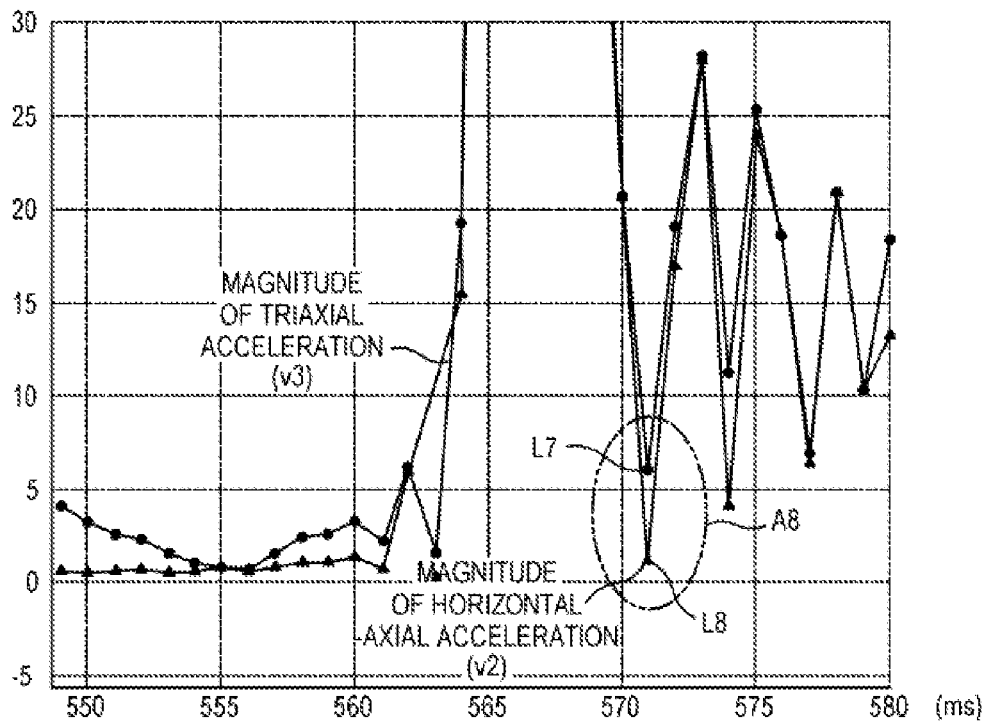
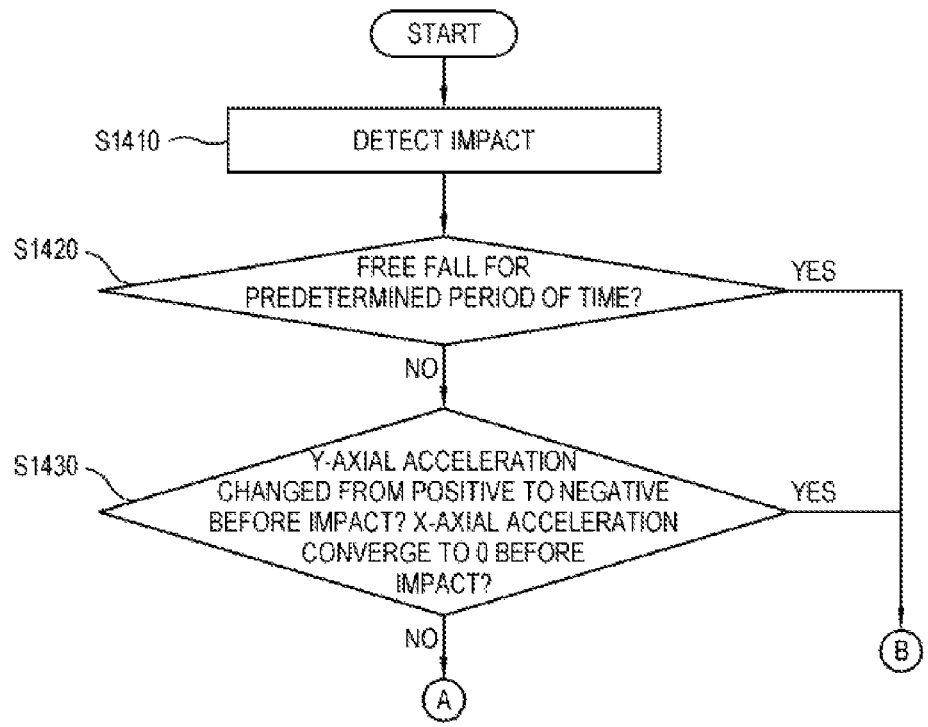

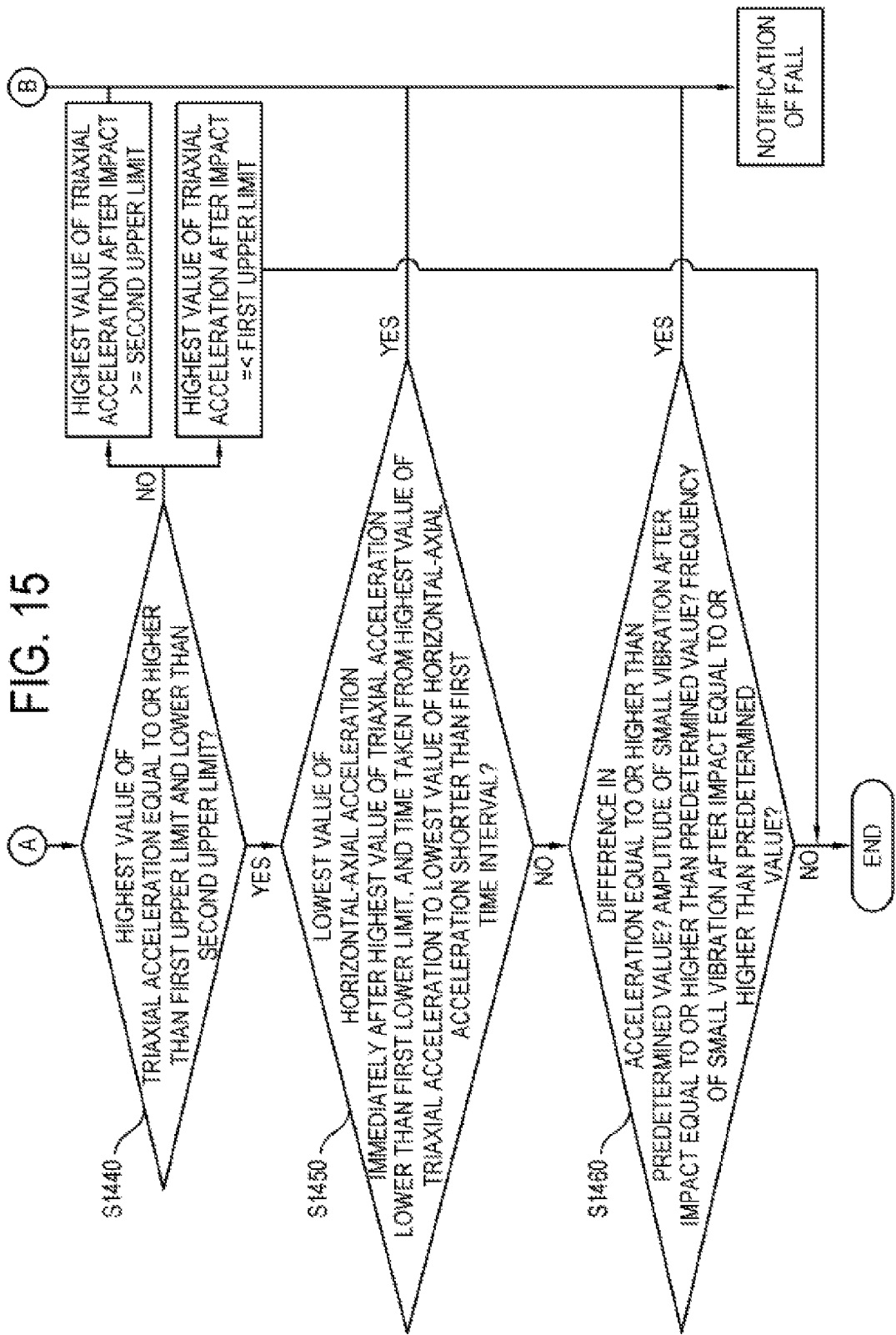

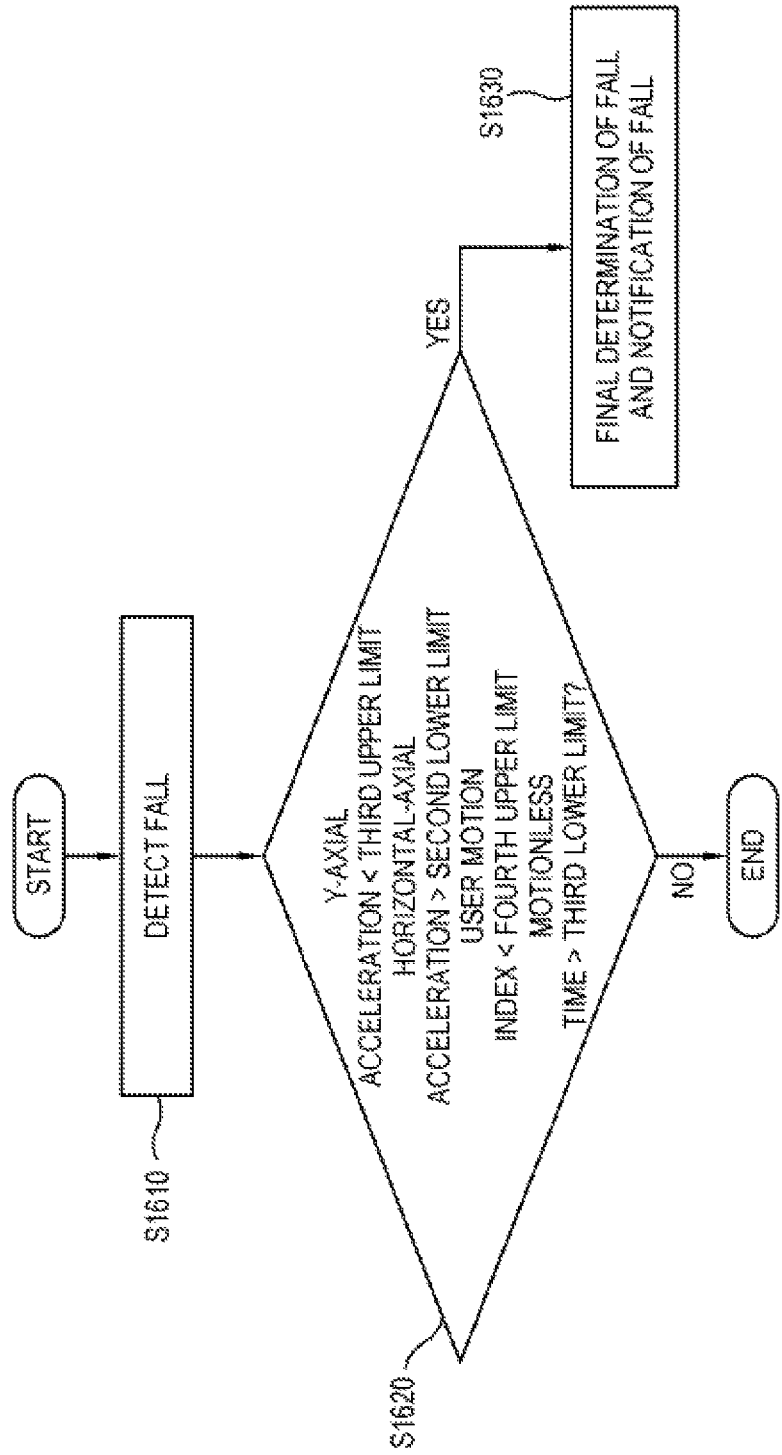

FALL DETECTION DEVICE AND METHOD FOR CONTROLLING THEREOF

TECHNICAL FIELD

The present invention relates to a fall detection device for determining whether a user gets hurt from a fall and a control of controlling the same, and more particularly to a fall detection device for determining whether a user gets hurt from a fall based on a motion of the fall detection device attached to the user.

BACKGROUND ART

A fall refers to an accident that a human gets hurt as unintentionally moving or falling down from his/her upright position to a lying position on the ground. Young people generally fall forward, whereas old people generally fall backward more dangerously than forward. The backward fall is likely to cause a fracture, and the fracture may lead to mental and physical malfunctions, thereby having a potential risk of shortening lifespan.

When a user falls backward, it undergoes a step of gradually decreasing the acceleration of gravity gradually decreases to 0 from time when the user starts falling down, a step of generating a peak of acceleration due to impact caused by collision with the ground, and a step of generating a small vibration after generating the peak of acceleration due to the impact. Conventionally, an acceleration sensor is attached to a user's body, and it is determined that a user falls backward when the acceleration of gravity decreases to be lower than or equal to a predetermined value before the impact due to the backward fall. As necessary, it is determined whether a user falls or not by checking time during which the peak of the acceleration lasts, the strength of the small vibration after the peak of the acceleration, and a lasting time of the small vibration. Further, to enhance the accuracy of determining whether a user falls down or not, fallen data sensed by the acceleration sensor may be collected and subjected to big data analysis through machine learning, a gyroscope's own feature points may be used along with each step of using the acceleration sensor, or a barometer may be used to sense relative change in height between before and after falling down to thereby determine a hurt from a fall.

DISCLOSURE

Technical Problem

However, such a conventional method of determining a hurt from a fall not only excessively increases memory usage and power consumption, but also increases an error rate in recognizing the hurt from the fall.

Technical Solution

Accordingly, there are provided a fall detection device capable of not only reducing memory usage and power consumption but also improving a fall recognition rate, and a method of controlling the same.

To achieve the foregoing objects, a fall detection device according to the present invention includes at least one sensor which is attached to a user and senses a motion of the fall detection device in a plurality of coordinate axial directions; an output section which outputs fall information of a user; and a controller which determines that the user falls down when acceleration in a first axial direction previously set among the plurality of coordinate axial directions is changed from a positive value to a negative value based on the motion of the fall detection device sensed by the sensor, and controls the output section to output the corresponding fall information. Thus, it is possible to reduce memory usage and power consumption, and improve a fall recognition rate.

The first axial direction may be perpendicular to the ground.

The controller may determine that impact occurs to the user before time of a first upper limit when acceleration of motion components on first axis-second axis-third axis among the plurality of coordinate axes is equal to or higher than the first upper limit.

The controller may determine that the user falls down when acceleration in a second axial direction among the plurality of coordinate axes is lower than a first lower limit before the impact occurs, in the case where the acceleration in the first axial direction is changed from the positive value to the negative value.

The controller may determine that the user falls down when acceleration of a motion component on a second axis-third axis plane is lower than or equal to a second lower limit after the impact occurs, in the case where the acceleration in the first axial direction is changed from the positive value to the negative value.

It may be determined that the user falls down when time elapsed until the acceleration of the motion component on the second axis-third axis plane reaches the second lower limit after the impact occurs is within a first threshold.

The output section may include a communicator for transmitting the fall information to an external device.

To achieve the foregoing objects, a method of controlling a fall detection device according to the present invention includes sensing a motion of the fall detection device in a plurality of coordinate axial directions as being attached to a user; determining that the user falls down when acceleration in a first axial direction previously set among the plurality of coordinate axial directions is changed from a positive value to a negative value based on the sensed motion of the fall detection device; and outputting corresponding fall information. Thus, it is possible to reduce memory usage and power consumption, and improve a fall recognition rate.

The first axial direction may be perpendicular to the ground.

The determining of that the user falls down may include determining that impact occurs to the user before time of a first upper limit when acceleration of motion components on first axis-second axis-third axis among the plurality of coordinate axes is equal to or higher than the first upper limit.

The determining of that the user falls down may include determining that the user falls down when acceleration in a second axial direction among the plurality of coordinate axes is lower than a first lower limit before the impact occurs, in the case where the acceleration in the first axial direction is changed from the positive value to the negative value.

The determining of that the user falls down may include determining that the user falls down when acceleration of a motion component on a second axis-third axis plane is lower than or equal to a second lower limit after the impact occurs, in the case where the acceleration in the first axial direction is changed from the positive value to the negative value.

The determining of that the user falls down may include determining that the user falls down when time elapsed until the acceleration of the motion component on the second axis-third axis plane reaches the second lower limit after the impact occurs is within a first threshold.

The method may further include transmitting the fall information to an external device.

Advantageous Effects

According to the present invention, there are provided a fall detection device capable of reducing memory usage and power consumption, and improving a fall recognition rate, and a method of controlling the same.

DESCRIPTION OF DRAWINGS

FIGS. 12 and 13 are graphs of triaxial acceleration and horizontal-axis acceleration when a human falls down backward and when a mannequin falls down backward, respectively.

FIGS. 14 to 16 are flowcharts of determining a fall.

BEST MODE

Below, embodiments of the present invention will be described with reference to accompanying drawings. However, the embodiments are not construed as limiting the present invention. Terms used in this specification are used just for describing one specific embodiment without limiting the scope of other embodiments.

Figure 1:
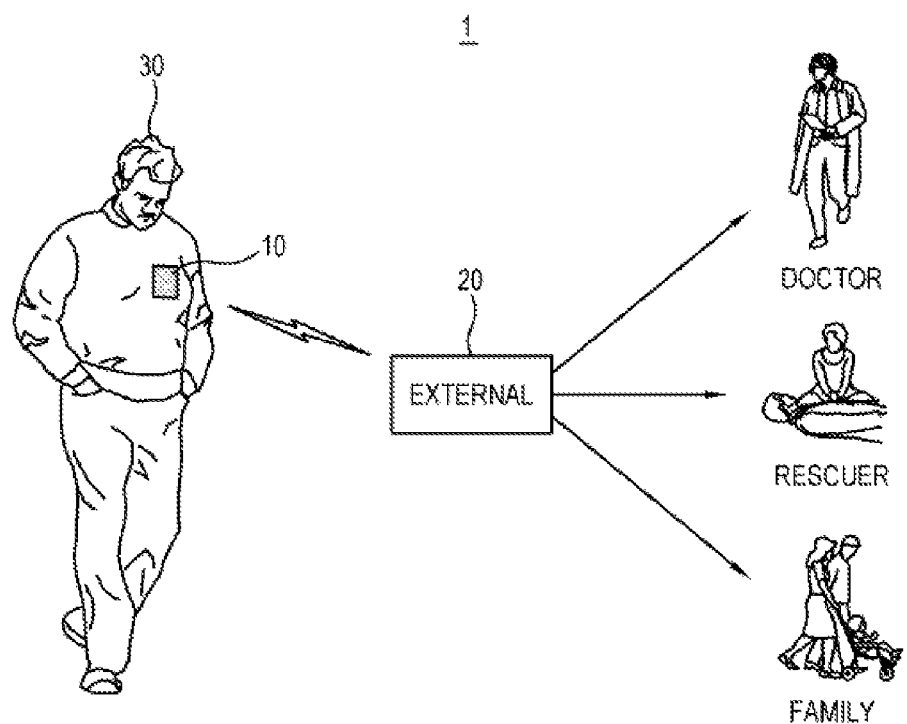
FIG. 1 illustrates an example of showing a fall detection system according to one embodiment of the present invention.

FIG. 1 illustrates an example of showing a fall detection system 1 according to one embodiment of the present invention. In the fall detection system 1 of FIG. 1, a user 30 may attach a fall detection device 10 around his/her chest. The more the fall detection device 10 is distant from the ground, the less an error rate is in recognizing a fall. Preferably, the fall detection device may be attached to a hat or glasses of a user 30. Hereinafter, it will be described on the assumption that the fall detection device 10 is provided in the form of a patch directly attached around a chest of a user 30.

A patch-type fall detection device 10 includes a built-in triaxial acceleration sensor. When the triaxial acceleration sensor 10 senses variation in triaxial acceleration in activities of a user 30, the fall detection device 10 determines a fall based on the sensed variation in the triaxial acceleration, and transmits a fall signal to an external device 20 in accordance with determination results. Here, the external device 20 may include a smart phone or a display device of others except a user 30, or a wireless pager or the like capable of making a warning sound. When the external device 20 receives the fall signal from the fall detection device 10, the display device displays a fall fact or the warning sound is made, thereby making others quickly rescue a user 30. In this case, others except a user 30 are previously set to prepare for a fall, and may for example include a family, a designated hospital and doctor, emergency medical center, etc.

Figure 2:
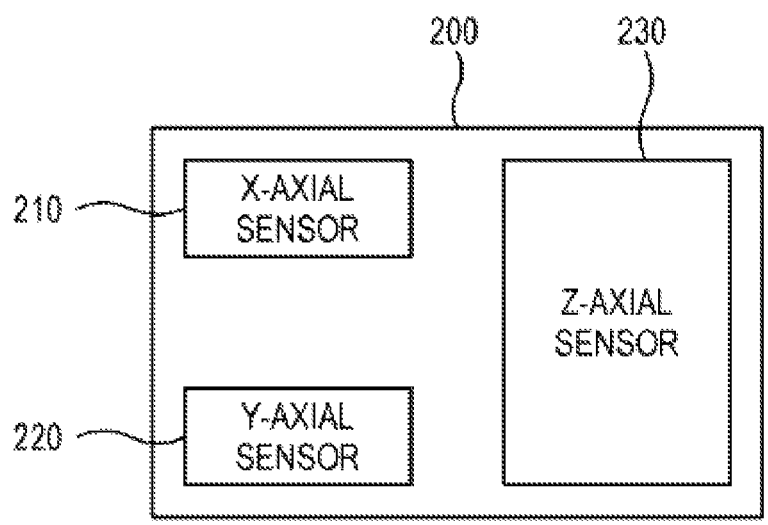
FIG. 2 is a block diagram of a triaxial acceleration sensor of a fall detection device in FIG. 1.

FIG. 2 is a block diagram of a triaxial acceleration sensor of the fall detection device 10 in FIG. 1. Referring to FIG. 2, a triaxial acceleration sensor 200 is internally provided in the fall detection device 10, and may include a servo type, a piezoelectric type, a piezoresistive type, an electrostatic capacitive type, etc. Specifically, the triaxial acceleration sensor 200 applies a force (F=ma) to a movable object with a certain mass m to be accelerated at an acceleration a, and measures a control signal, a piezoelectric pressure, an electrostatic capacity, and the like varied depending triaxial displacement of the movable object, thereby obtaining the triaxial acceleration. To this end, the triaxial acceleration sensor 200 may include an X-axial acceleration sensor 210, a Y-axial acceleration sensor 220, and a Z-axial acceleration sensor 230. As necessary, the triaxial acceleration sensor 200 may include a triaxial micro electro-mechanical system (MEMS) acceleration sensor. That is, acceleration in each axial direction is measured based on a phenomenon that a cooling degree of a heating element caused by heat convection of fluid, gas, liquid, etc. depends on the direction and magnitude of acceleration.

Figure 3:
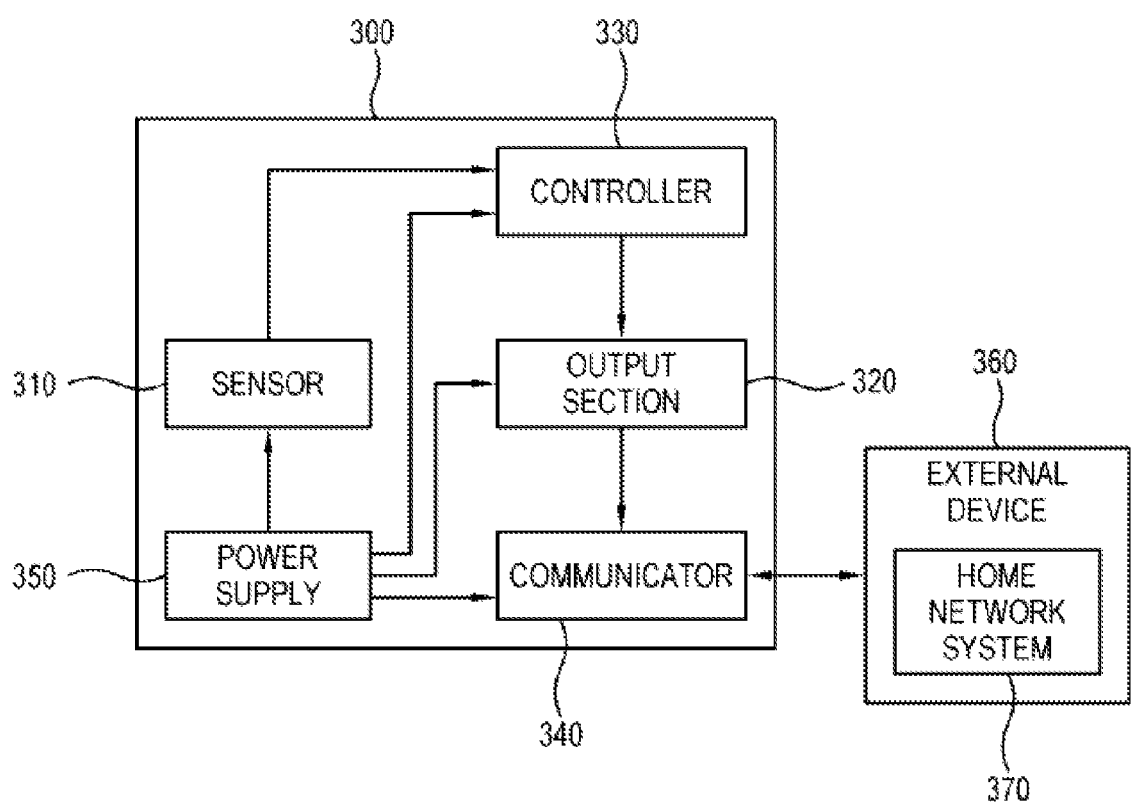
FIG. 3 is a block diagram of showing the fall detection device of FIG. 1.

FIG. 3 is a block diagram of showing the fall detection device of FIG. 1. The fall detection device 300 of FIG. 3 corresponds to the fall detection device 10 of FIG. 1, and repetitive descriptions will be avoided. Referring to FIG. 3, the fall detection device 300 includes at least one sensor 310 which is attached to a user 30 and senses motions of the fall detection device 300 in a plurality of coordinate axes, an output section 320 through which information about a fall of a user is output, and a controller 330 controls the output section 320 to output corresponding fall information by determining that the user falls down when acceleration in a preset first axial direction among the plurality of coordinate axes is changed from a positive value to a negative value based on the motion of the fall detection device 300 sensed through the sensor 310.

Here, the first axial direction may be perpendicular to the ground. For example, when a user 30 stands on the ground, the first axial direction may refer to a head-axial direction of a user 30 perpendicular to the ground. The second axial direction perpendicular to the first axial direction may refer to a frontward direction of the user 30, and the third axial direction perpendicular to both the first axial direction and the second axial direction may refer to a leftward direction of the standing user 30.

The controller 330 may be achieved by a central processing unit (CPU) or a processor, and typically control operations of elements to thereby control general operations of the fall detection device 300. The sensor 310 may include not only the triaxial acceleration sensor 200 but also an electrocardiography (ECG) sensor. As necessary, an acceleration signal measured by the triaxial acceleration sensor 200 may be used as a signal for measuring the metabolism and ECG of the user 30. The output section 320 may further include a communicator 340 for transmitting the fall information to an external device 360. When the controller 330 determines a fall, the external device 360 can be informed of a fall fact through the communicator 340. A power supply 350 may include a battery, and receives external or internal power and supplies power needed for operating the elements under control of the controller 330. The sensor 310 senses whether or not the fall detection device 300 is attached to a user. When the user 30 does to attach or detaches the fall detection device 300, the sensor 310 senses it and informs the controller 330 of the detachment of the fall detection device 310. In this case, the controller 330 may control the power supply 350 not to supply the power to the elements until the user 30 attaches the fall detection device 300 onto him/her.

By the way, the external device 360 includes a home network system 370. The home network system 370 includes a plurality of home devices and home gateways having control and communication functions. The home devices may be placed inside and outside a home of the user 30, and include smart appliances, security devices, lighting devices, energy devices, etc. The smart appliances may include a television (TV), an air conditioner, a robot cleaner, a humidifier, etc. The security devices may include a door lock, a security camera, a closed circuit television (TV), a security sensor for sensing a touch, a sound, a motion and the like, etc. The lighting devices may include a light emitting diode (LED), a lamp, etc. The energy devices may include a heating device, a power meter, a power socket, an electric outlet, a multiple-tap, etc.

Such home devices may be configured to communicate with home gateways in accordance with wired or wireless communication methods, receive a control command from the home gateway, operate in response to the control command, and transmit requested information and/or data to the home gateway. The home gateway may be materialized by an independent device or a device having a function of the home gateway. For example, the home gateway may be materialized by a TV, a cellular phone, a tablet computer, a set-top box, a robot cleaner, or a personal computer. The home gateway includes corresponding communication modules for communicating with the home devices in accordance with a wired or wireless communication method, registers and stores information about the home devices, manages and controls the operations, supportable functions and states of the home devices, and collects and stores necessary information from the home devices. In particular, the home gateway connects with a data network such as Internet, i.e. an internet protocol (IP) network, allows the communicator 340 of the fall detection device 300 to have an access thereto through the Internet, and transmits a notice signal from the communicator 340 to a corresponding home device. Further, the home gateway may communicate with the communicator 340 through wireless fidelity (Wi-Fi), Zigbee, Bluetooth, near field communication (NFC), z-wave and the like wireless communication methods.

The home network system 370 provides information about a location of the user 30 and a medium of the ground to the fall detection device 300, and makes the user 30 prepare for a fall. The home network system 370 may be applicable to not only a home but also any space such as a hospital, an office, and the like where the user 30 lives.

Figure 4:
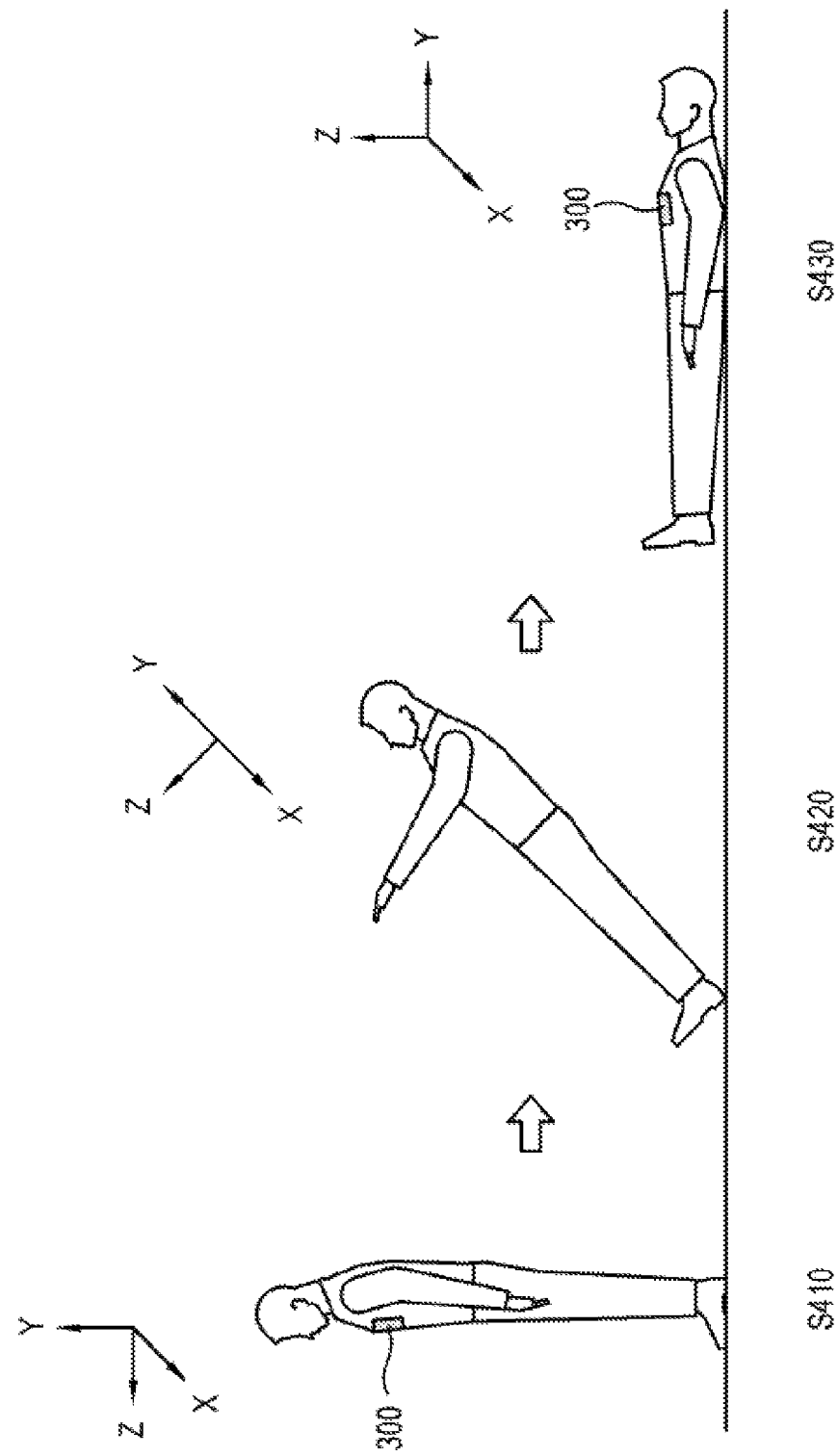
FIG. 4 illustrates an example of showing a falling procedure.

FIG. 4 illustrates an example of showing a falling procedure. Referring to FIG. 4, the falling procedure includes a first section S410 where the user 30 is erectly standing on the ground, a second section S420 from a moment when the user 30 starts falling backward to a moment just before the user 30 collides with the ground, and a third section where the user 30 collides with the ground.

In the first section S410, the user 30 attached with the fall detection device 300 is usually upright on the ground. In this case, it will be defined that the acceleration of gravity acts in a Y-axial direction, the front side of the user 30 tends a Z-axial direction and the left side of the user 30 tends to an X-axial direction. However, the following descriptions may be varied depending on how the coordinate system of the user 30 is defined with regard to the fall detection device 300, and feature points of a fall to be discussed below in determining the fall may be interpreted by the same method regardless of the defined coordinate system. In the first section S410, acceleration in the Y-axial direction has a positive value corresponding to the acceleration of gravity, and acceleration in the Z-axial direction and acceleration in the X-axial direction, which are on planes perpendicular to the acceleration of gravity, respectively have values of 0.

The second section S420 is in between the moment when the user 30 loses his/her consciousness or footing and starts falling backward and the moment just before the user 30 collides with the ground. The acceleration in the Z-axial direction is varied depending on whether the user is conscious or not from the moment when the user 30 starts falling. For example, when the user 30 braces himself/herself against falling, the acceleration in the Z-axial direction temporarily increases from 0 to a positive direction by the acceleration of gravity, but converges to 0 by free fall at the moment when the user 30 completely loses his/her consciousness and falls down. However, when the user 30 loses his/her consciousness and falls down from the start, the acceleration in the Z-axial direction initially approximates to 0. The acceleration in the Y-axial direction converges to 0 from a positive value corresponding to the acceleration of gravity, and then changes into a negative value by centrifugal force. That is, impact caused by the collision with the ground occurs after the acceleration in the Y-axial direction is changed into the negative value. Here, the negative acceleration is caused by the centrifugal force generated when the user 30 falls down, and particularly refers to a feature point of a fall when the user 30 loses his/her consciousness and falls down. Therefore, it is possible to determine whether the user 30 falls down or not based on whether the acceleration in the Y-axial direction is changed from the positive value to the negative value. Since this feature point of a fall, i.e. the change of the acceleration in the Y-axial direction from the positive value to the negative value is unusual in daily life, an error rate in recognizing the fall is noticeably lowered when the fall is determined based on this feature point.

In the third section S430, the acceleration has a peak value and small vibration occurs because of the collision between the user 30 and the ground. Here, the magnitude of the acceleration refers to a square root of the sum of respective squares of accelerations in the X-axial direction, the Y-axial direction and the Z-axial direction, and defined as an acceleration of motion components on the first axis (X-axis)—second axis (Y-axis)—third axis (Z-axis). Further, the peak value in the magnitude of the acceleration refers to the highest value in the magnitude of the acceleration after the impact. When the small vibration stops, the acceleration in the Z-axial direction is sensed as a value corresponding to the negative acceleration of gravity, and the acceleration in the X-axial direction and the acceleration in the Y-axial direction parallel with a horizontal plane of the ground converge to 0.

FIG. 4 illustrates when the user 30 falls within a plane formed by the Y-axis and the Z-axis. The features that the acceleration in the Y-axial direction has the negative value by the centrifugal force in FIG. 4 are also extensively applied to an arbitrary direction in which the user 30 loses the consciousness and falls down. This is because it is possible to determine whether the user 30 falls down or not by sensing the acceleration of each axial direction in a coordinate system newly defined through coordinate transformation from the existing coordinate system as long as the new coordinate system is defined to make the user 30 fall within a plane formed by the Y-axis and the Z-axis.

Figure 5:
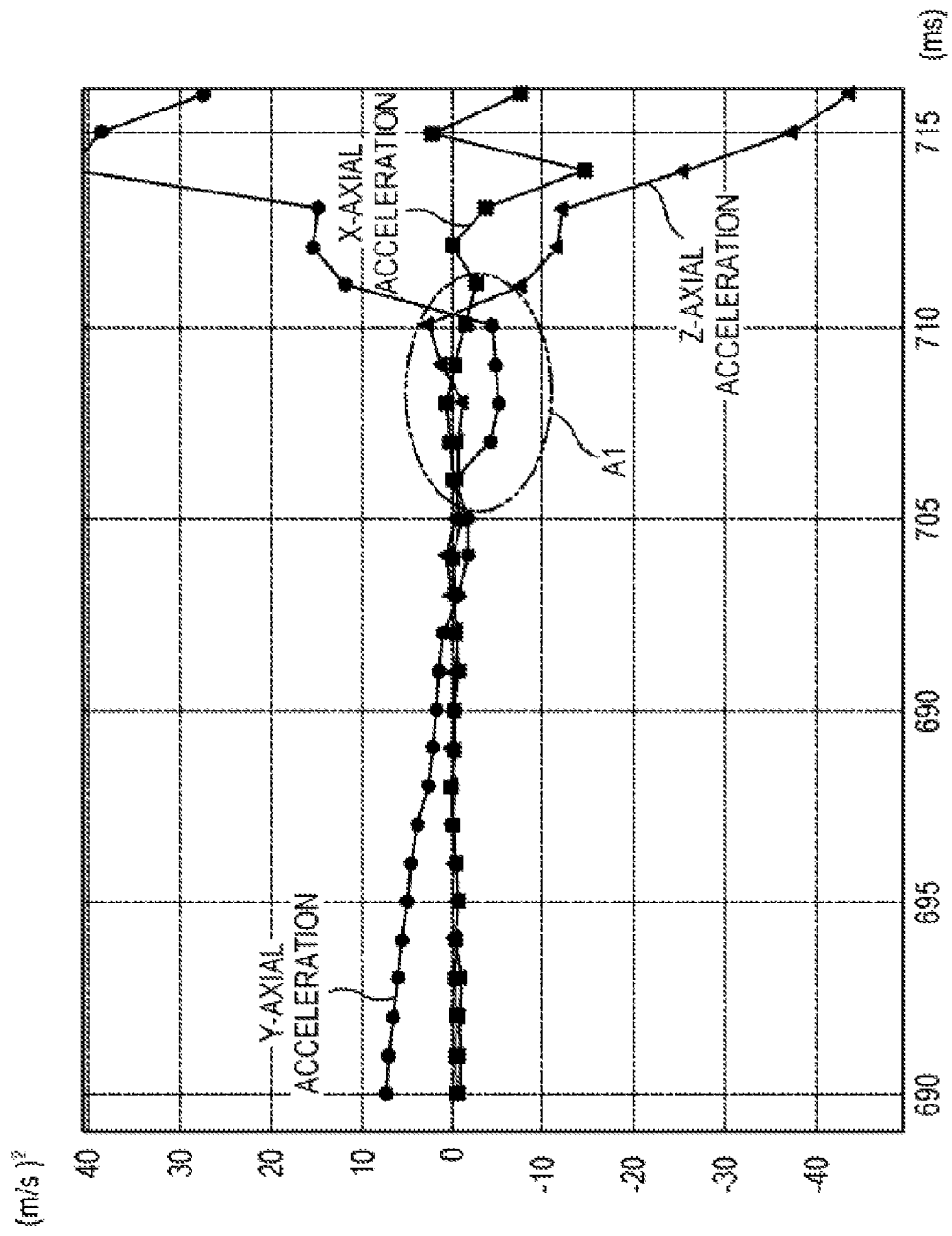
FIG. 5 is a graph of showing triaxial acceleration measured in experiments when a human falls backward.

FIG. 5 is a graph of showing triaxial acceleration measured in experiments when a human falls backward. Referring to FIG. 5, in the first section S410, acceleration in the Y-axial direction of a human 30 has a positive value corresponding to the acceleration of gravity, but acceleration in the Z-axial direction and acceleration in the X-axial direction approximate to 0 since a Z-X plane is parallel with the ground. In the second section S420, the acceleration in the Y-axial direction converges to 0 and is then changed into a negative value (A1) because the acceleration of gravity acting in the Y-axial direction decreases but the centrifugal force in the opposite direction to the Y-axial direction increases while the human 30 falls down. In more detail, when a mass m of the user 30, a height r from the ground to a triaxial acceleration sensor 300, an angular velocity w when the user 30 falls, and the acceleration of gravity g are taken into account, the centrifugal force is greater than the gravity ($mrw^2$>mg) in the area A1 where the acceleration in the Y-axial direction is changed into the negative value.

Such a phenomenon occurs before impact when the impact is caused as the human 30 falls down by losing his/her consciousness and collides with the ground, but rarely occurs in daily life. This is because the minimum acceleration in each axial direction is 0 unless the human 30 is pushed by external force.

Referring back to FIG. 5, the acceleration in the Y-axial direction was measured as about −5 m/s$^2$ in the area A1 where the acceleration in the Y-axial direction is changed into the negative value. However, the measured value may be varied since the height from the ground to the position to which the fall detection device 300 is attached is different according to the heights of the users 30. For example, when the fall detection device 300 is attached around the chest, the acceleration in the Y-axial direction measured in the area A1 where the acceleration in the Y-axial direction is changed into the negative value (hereinafter, referred to as a "threshold of acceleration in the Y-axial direction") may be measured as lower when a tall user 30 falls down than that measured when a short user 30 falls down. Therefore, the threshold of the acceleration in the Y-axial direction for the tall user 30 is set to be lower than that for the short user 30, thereby enhancing the fall recognition rate according to the heights of the users 30.

By the way, an acceleration signal sensed by the triaxial acceleration sensor 200 of the fall detection device 300 may be used as a signal for measuring the ECG, and therefore the triaxial acceleration sensor 200 may be employed as an ECG sensor. Thus, the threshold of the acceleration in the Y-axial direction is properly set by taking body information of the user 300, for example, age, chronic diseases, arthritis, muscle mass, heart disease, and whether the sense of balance is lost due to drug-taking, into account, based on the ECG of the user 30 to which the fall detection device 300 is attached, thereby improving the fall recognition rate in accordance with the body information of the user 30.

As described above, the change of the acceleration in the Y-axial direction from the positive value to the negative value is regarded as a feature point of a fall according to the present invention, and only the acceleration sensor is enough to sense the feature point, thereby consuming lower power to provide a fall detection service than that of using a gyroscope or other fall detection devices.

Figure 6:
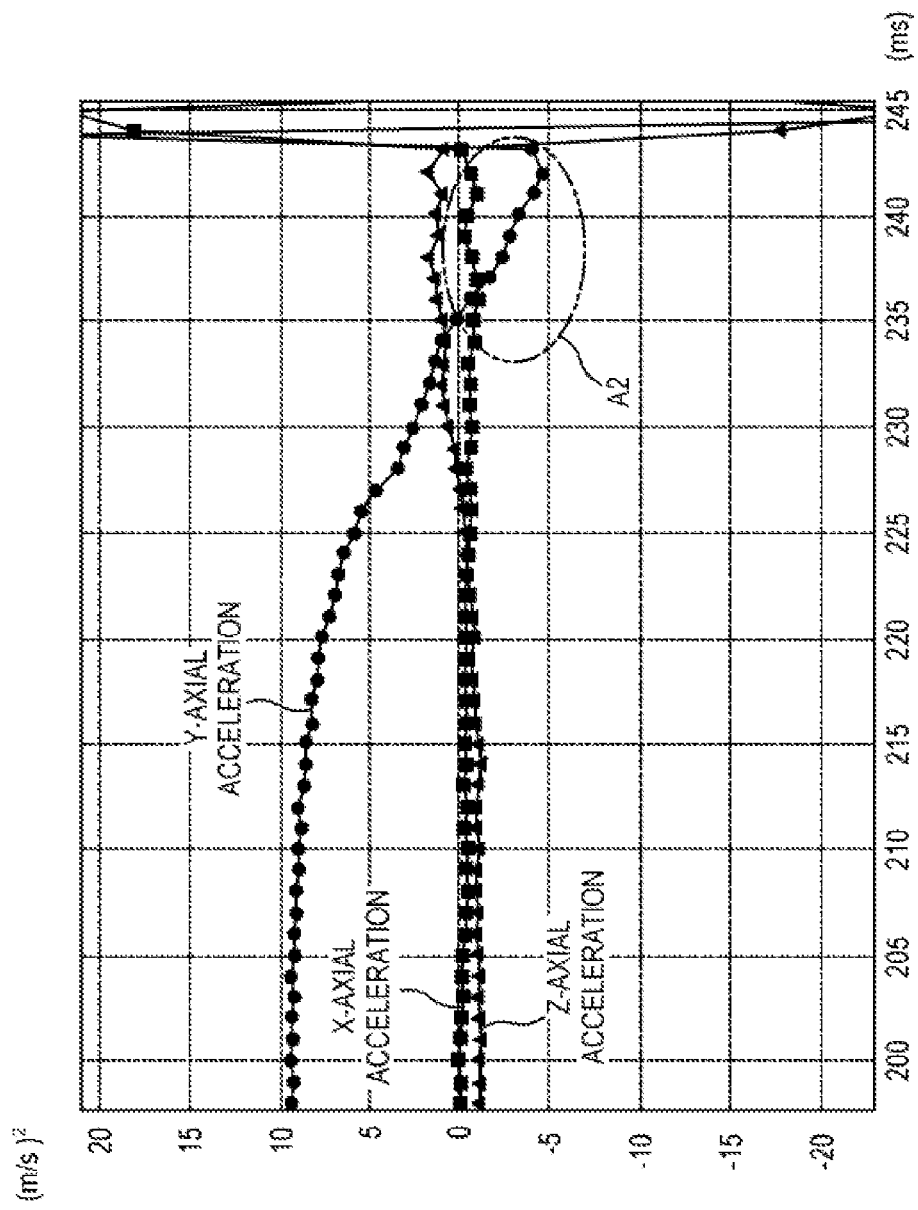
FIG. 6 is a graph of triaxial acceleration measured by experiments when a mannequin falls backward.

FIG. 6 is a graph of triaxial acceleration measured by experiments when a mannequin falls backward. Like that the human 30 falls backward as shown in FIG. 5, the acceleration sensor senses that the acceleration in the Y-axial direction converges to 0 from the positive value corresponding to the acceleration of gravity and then enters a negative area A2 even when a mannequin 30 falls backward. Further, the acceleration sensor may sense that the acceleration in each axial direction shows a peak value due to impact caused by collision between the mannequin 30 and the ground. In this case, the controller determines that the mannequin 30 falls down based on that the acceleration in the Y-axial direction enters the negative area A2 just before the peak value.

FIGS. 5 and 6 respectively show that the human and the mannequin fall backward, but the present invention may be applied to even when the human and the mannequin fall forwards and sideways. For example, in even case where the human and the mannequin fall forward, it may be determined that the human and the mannequin get hurt from forward falls when the acceleration in the head-axial direction, i.e. the acceleration in the Y-axial direction is changed from a positive value to a negative value, and the sign of the acceleration in the Z-axial direction is sensed as opposed to the sign of the acceleration in the Z-axial direction due to impact at the backward fall.

Figure 7:
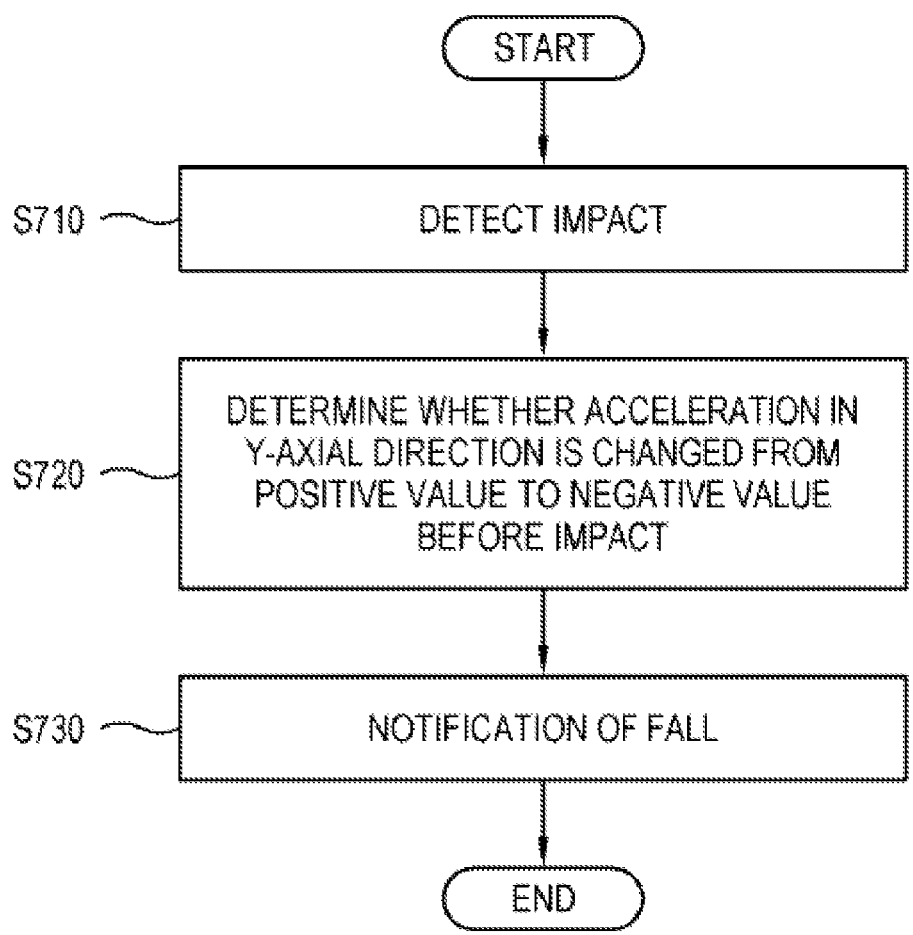
FIG. 7 is a flowchart of a fall detection method of using the fall detection device of FIG. 3.

FIG. 7 is a flowchart of a fall detection method of using the fall detection device of FIG. 3. Referring to FIG. 7, the fall detection device 300 includes the triaxial acceleration sensor 310, and thus senses triaxial acceleration in a motion of a user 30 who wears the fall detection device 300. At least one sensor of the triaxial acceleration sensor 310 senses that impact occurs to the user 30 (S710). In this case, the peak value of the acceleration in each axial direction may be used to determine whether the impact occurs or not.

However, it is unclear whether the impact is caused by the fall or not. Therefore, the fall detection device 300 determines whether the acceleration in the head-axial direction of the user 30, i.e. the acceleration in the Y-axial direction is changed from a positive value to a negative value just before the impact (S720). When the acceleration in the head-axial direction of the user 30, i.e. the acceleration in the Y-axial direction is changed from a positive value to a negative value just before the impact, the fall detection device 300 determines that the user 30 falls down, and outputs a fall fact to the external device 20 (S730).

As necessary, the fall detection device 300 may not perform the operation S710 of detecting whether the impact occurs to the user 30, but only determine the fall based on whether the acceleration in the head-axial direction of the user 30, i.e. the acceleration in the Y-axial direction is changed from a positive value to a negative value and the acceleration in a horizontal-axial direction, i.e. the acceleration in the Z-axial and the X-axial directions approximates to 0 (S720). In this regard, descriptions will be made in more detail with reference to FIGS. 8 and 9.

Figure 8:
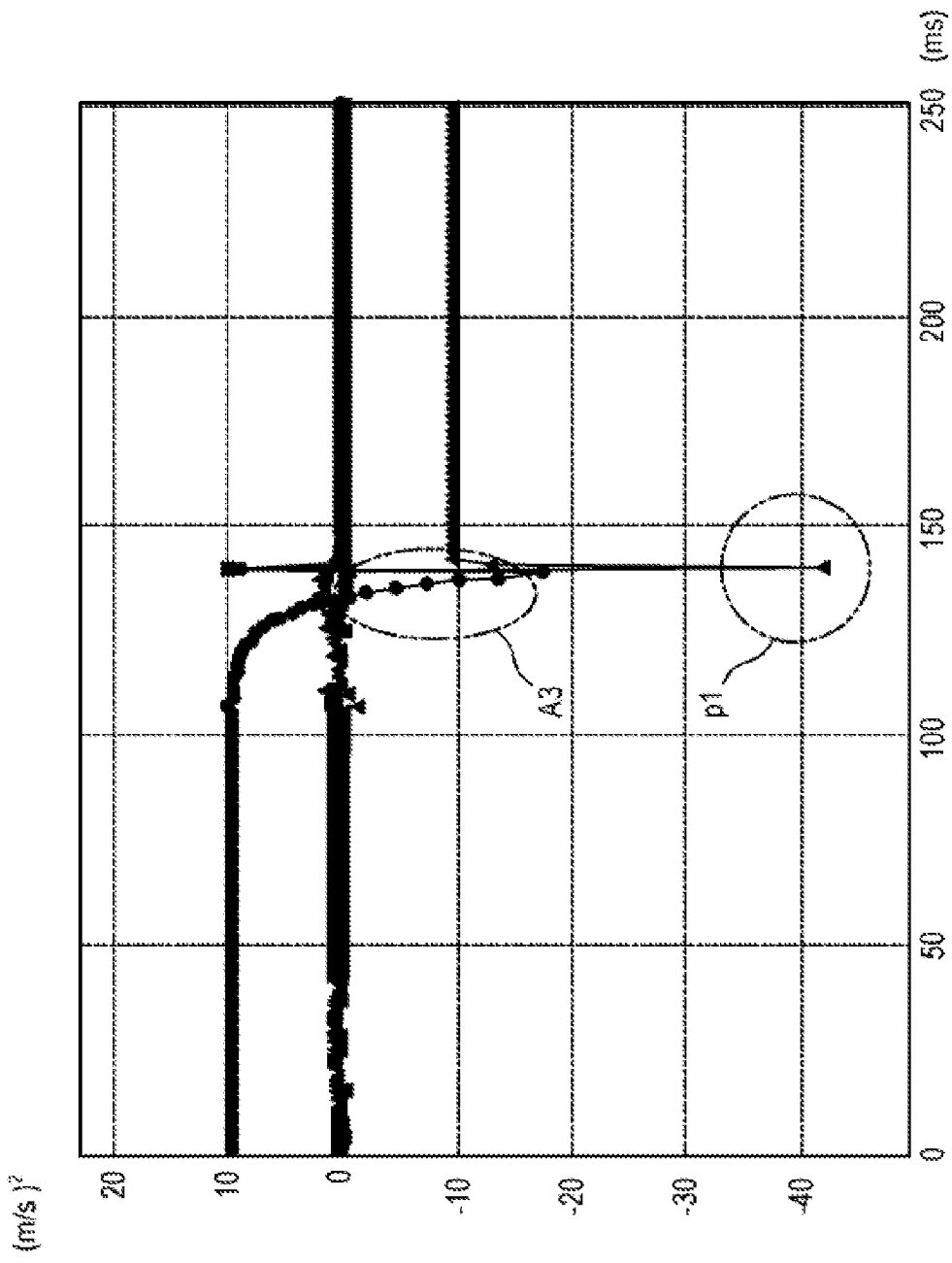
FIGS. 8 and 9 are graphs of when a peak value caused by collision between a user and the ground when the user falls backward is sensed and when no peak values are sensed.
Figure 9:
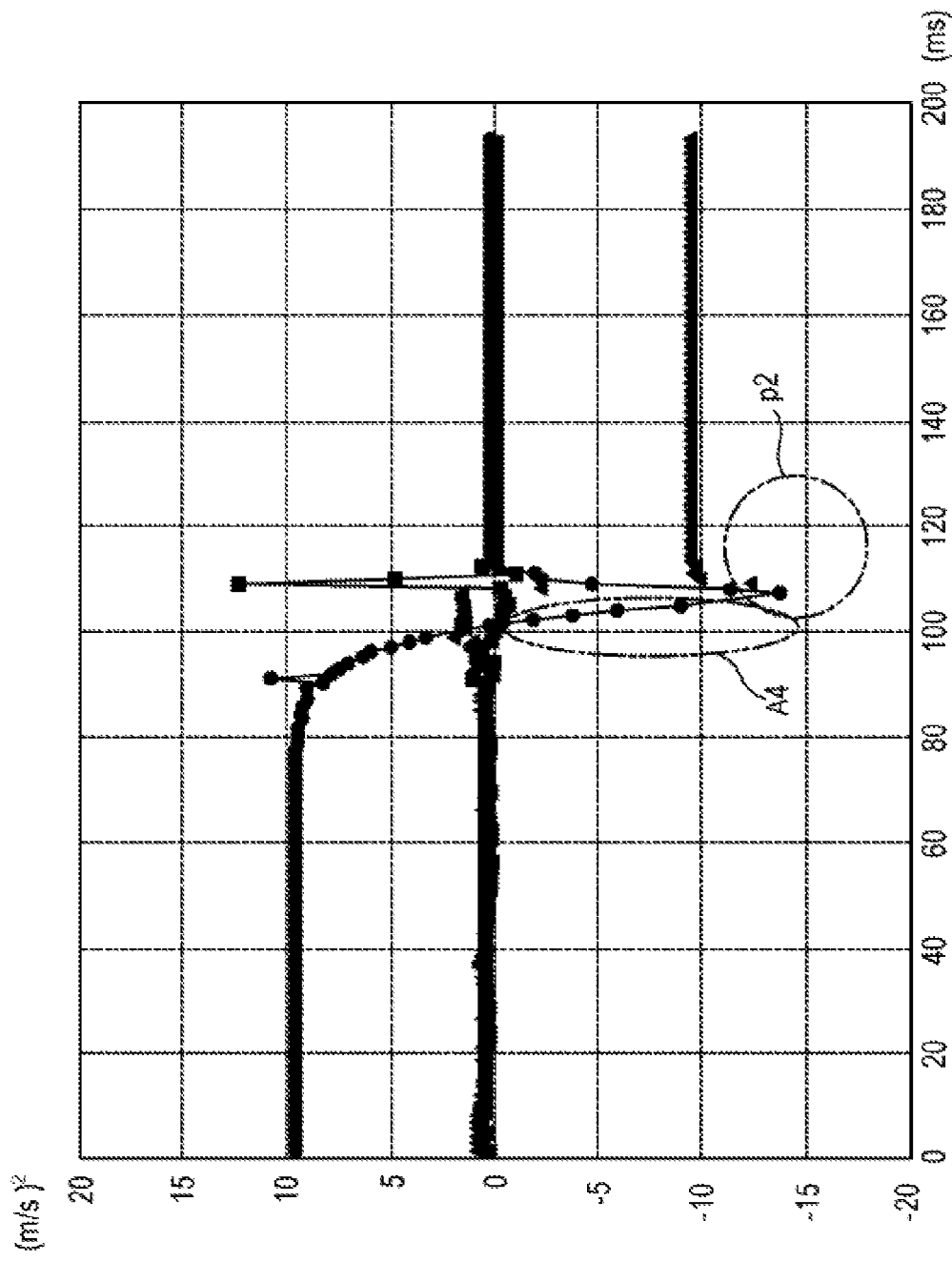

FIGS. 8 and 9 are graphs of when a peak value caused by collision between a user and the ground when the user falls backward is sensed and when no peak values are sensed. First, referring to FIG. 8, when a feature point A3 for determining a fall and a peak value P1 are sensed together in the area where the acceleration in the Y-axial direction is changed from a positive value to a negative value, the fall detection device 300 may determine that the user 30 gets hurt from a fall.

On the other hand, referring to FIG. 9, a peak value P2 caused by impact is not sensed, the reason of which is because sampling timing of the acceleration sensor is inadequate. Conventionally, the fall recognition rate is low since the fall is determined only when the peak value P1 caused by the impact is sensed as shown in FIG. 8 but not properly determined when the peak value P2 caused by the impact is not sensed as shown in FIG. 9. However, even when the peak value P2 caused by the impact is not sensed as shown in FIG. 9, the fall detection device 300 can determine whether the user 30 falls or not by detecting the area A4 where the acceleration in the Y-axial direction is changed from a positive value to a negative value and sensing whether the acceleration in the horizontal-axis direction, i.e. the acceleration in the Z-axial and X-axial directions approximate to 0. That is, the fall detection device 300 is capable of determining whether the user 30 falls or not regardless of the sampling timing of the sensor, and thus improved in the fall recognition rate.

Figure 10:
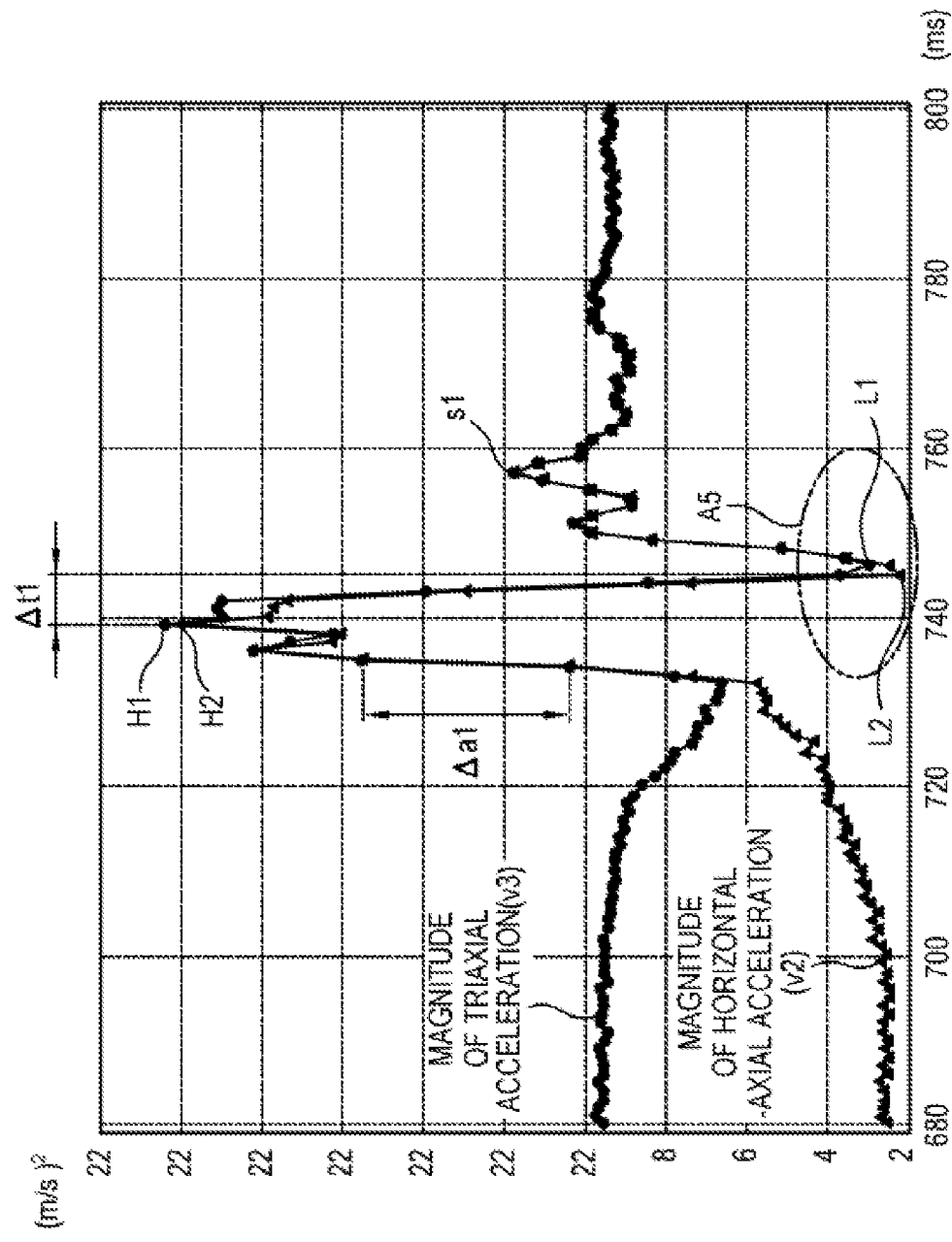
FIG. 10 is a graph of showing variation in acceleration when a user falls down backward.
Figure 11:
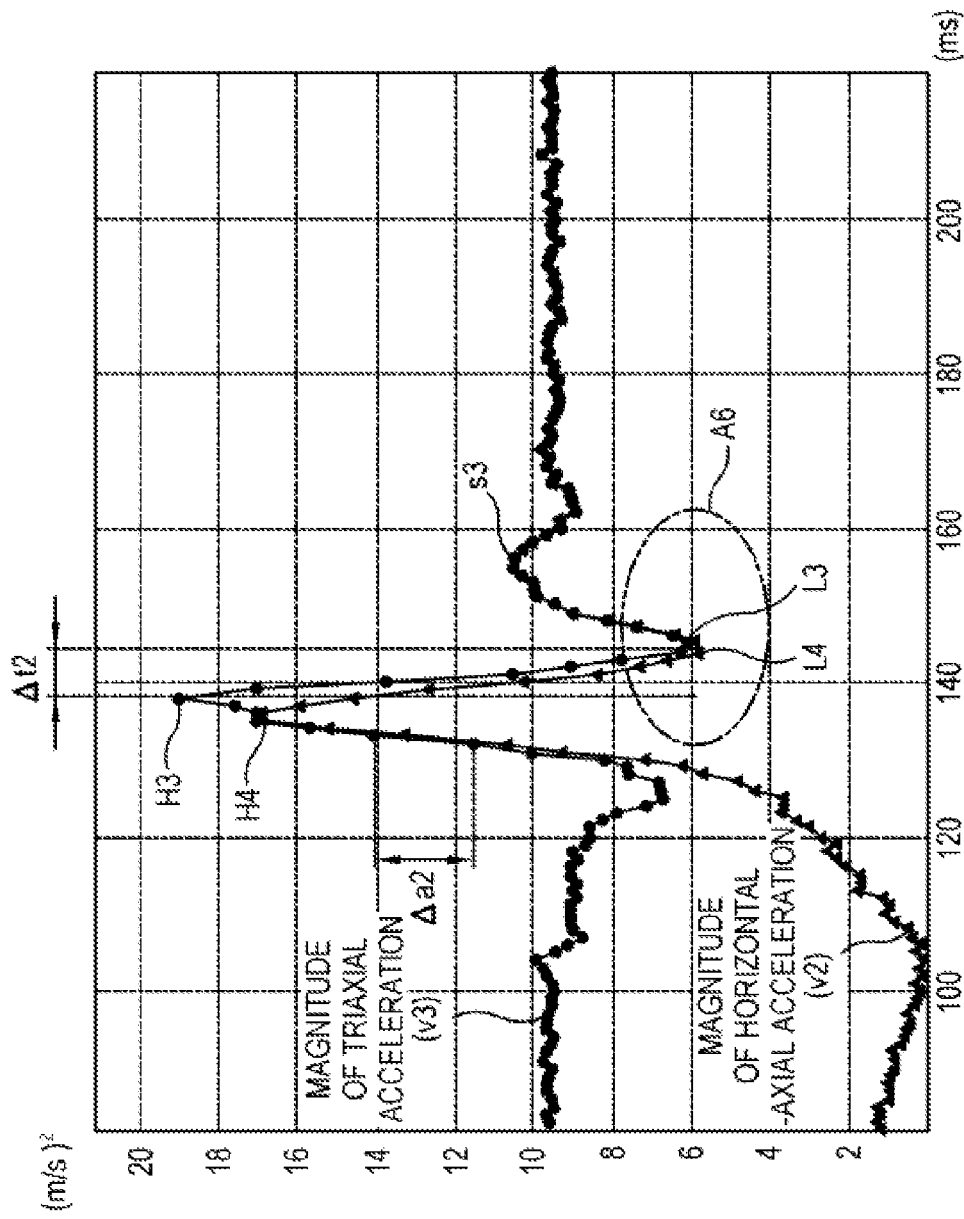
FIG. 11 is a graph of showing variation in acceleration when a user lies down backward.

FIG. 10 is a graph of showing variation in acceleration when a user falls down backward, and FIG. 11 is a graph of showing variation in acceleration when a user lies down backward. Conventionally, it is determined that the user 30 falls down when the peak value of the acceleration is equal to or higher than a first upper limit, and it is determined that the user 30 does not fall down when the peak value is lower than the second upper limit. By the way, it is not easy to determine whether the user 30 falls down or not when the maximum acceleration is in between the first upper limit and the second upper limit. In this case, it is possible to determine whether the user 30 falls or not based on whether the minimum magnitude of the horizontal-axis acceleration immediately after the first peak value of the acceleration caused by the impact of the fall is within the first lower limit.

Here, the magnitude v3 of the acceleration is defined by a square root ($v3=\sqrt{X^2+Y^2+Z^2}$) of the sum of respective squares of the acceleration in the X-axial direction (X), the acceleration in the Y-axial direction (Y) and the acceleration in the Z-axial direction (Z) of FIG. 4, and the magnitude v2 of the horizontal-axis acceleration is defined by a square root ($v2=\sqrt{X^2+Z^2}$) of the sum of respective squares of the accelerations in the X-axial direction and the Z-axial direction of FIG. 4. In other words, the magnitude v2 of the horizontal-axis acceleration) refers to acceleration of motion components of the user on X-Z plane.

Referring to FIG. 10, when the user 30 loses his/her consciousness and falls backward, the magnitude v3 of the triaxial acceleration gradually decreases as the acceleration in the Y-axial direction converges to 0 from a positive value corresponding to the acceleration of gravity, increases up to the highest value H1 due to the collision with the ground, and then rapidly decreases up to the lowest value L1. Further, when the user 30 loses his/her consciousness and falls backward, the magnitude v2 of the horizontal-axis acceleration increases up to the highest value H2 due to the collision with the ground and then decreases up to the lowest value L2.

Here, the feature point for determining whether the user 30 falls or not depends on whether the lowest value L2 of the magnitude v2 of the horizontal-axis acceleration immediately after the first highest value H1 of the magnitude v3 of the acceleration caused by the collision with the fall is within the first lower limit. The reason why the lowest value L2 of the magnitude v2 of the horizontal-axis acceleration is used instead of the lowest value L1 of the magnitude v3 of the acceleration immediately after the first highest value H1 of the magnitude v3 of the acceleration is because the magnitude the acceleration in the Y-axial direction is considerably large when the user 30 actually falls backward whereas the acceleration of gravity, i.e. the acceleration in the Z-axial direction is theoretically the largest among the magnitudes of the accelerations at the impact when the user 30 falls backward. That is, in the first area lower than the acceleration of gravity after the highest value H1 of the magnitude v3 of the triaxial acceleration, the acceleration in the Y-axial direction is sensed as greater than the horizontal-axis acceleration. This means that the magnitude v3 of the triaxial acceleration may be greater than the magnitude v2 of the horizontal-axis acceleration in the first area lower than the acceleration of gravity after the highest value H1 of the magnitude v3 of the triaxial acceleration.

Therefore, when the lowest value L2 of the magnitude v2 of the horizontal-axis acceleration is used instead of the lowest value L1 of the magnitude v3 of the acceleration immediately after the first highest value H1 of the magnitude v3 of the acceleration, it is possible to set the first lower limit to be low. That the first lower limit is lowered indicates that the error rate in recognizing a fall is lowered.

Meanwhile, referring to FIG. 11, in case where the user 30 lies backward, the magnitude v3 of the triaxial acceleration gradually decreases, and increases up to the highest value H3 and then decreases up to the lowest value L3 when impact is caused by collision between the user 30 and the ground, and the magnitude v2 of the horizontal-axis acceleration also increases up to the highest value H4 and then decreases up to the lowest value L4. By the way, the lowest value L3 of the magnitude v3 of the triaxial acceleration is a little greater than or similar to the lowest value L4 of the magnitude v2 of the horizontal-axis acceleration when the user 30 lies backward, but is generally greater than the lowest value L2 of the magnitude v2 of the horizontal-axis acceleration when the user 30 falls backward.

Accordingly, when the fall of the user 30 is determined based on whether the lowest value of the magnitude v2 of the horizontal-axis acceleration instead of the lowest value of the magnitude v3 of the triaxial acceleration is within the first lower limit, it is possible to lower the error rate in recognizing the fall that occurs in daily life.

By the way, the first highest value H1 of the magnitude v3 of the acceleration or the lowest value L2 of the magnitude v2 of the horizontal-axis acceleration may be differently measured in accordance with fallen positions and the kinds of medium of the ground at the fall. For example, the first highest value H1 of the magnitude v3 of the acceleration or the lowest value L2 of the magnitude v2 of the horizontal-axis acceleration is different between a case where the user 30 falls down on a mattress and the like protective mat and a case where the user 30 falls down on a marble floor. Therefore, the first highest value H1 of the magnitude v3 of the acceleration or the lowest value L2 of the magnitude v2 of the horizontal-axis acceleration is set to have a proper threshold in accordance with the fallen positions and the kinds of medium of the ground at the fall, thereby enhancing the fall recognition rate and lowering the fall recognition error.

Information about the fallen positions and the kinds of medium may be received by the communicator 340 from the home network system 370. That is, the home network system 370 may transmit information about the fallen positions and the kinds of medium, varied depending on movement of the user 30, to the communicator 340 in real time. The controller 330 may set the first highest value H1 of the magnitude v3 of the acceleration or the lowest value L2 of the magnitude v2 of the horizontal-axis acceleration to have a proper threshold, based on the information about the fallen positions and the kinds of medium received through the communicator 340.

Further, the fall detection device 300 may set the first highest value H1 of the magnitude v3 of the acceleration or the lowest value L2 of the magnitude v2 of the horizontal-axis acceleration to have a stepwise threshold, and the controller 330 may determine how seriously the user 30 gets hurt from a fall based on a degree of the first highest value H1 of the magnitude v3 of the acceleration or the lowest value L2 of the magnitude v2 of the horizontal-axis acceleration sensed by the sensor 310 at the fall. Therefore, the external device 360 can be stepwise informed of seriousness of a hurt together with a fall through the communicator 340, and thus a rescuer who is informed of the fall can take adequate rescue activities for the fallen user 30.

Figure 12:
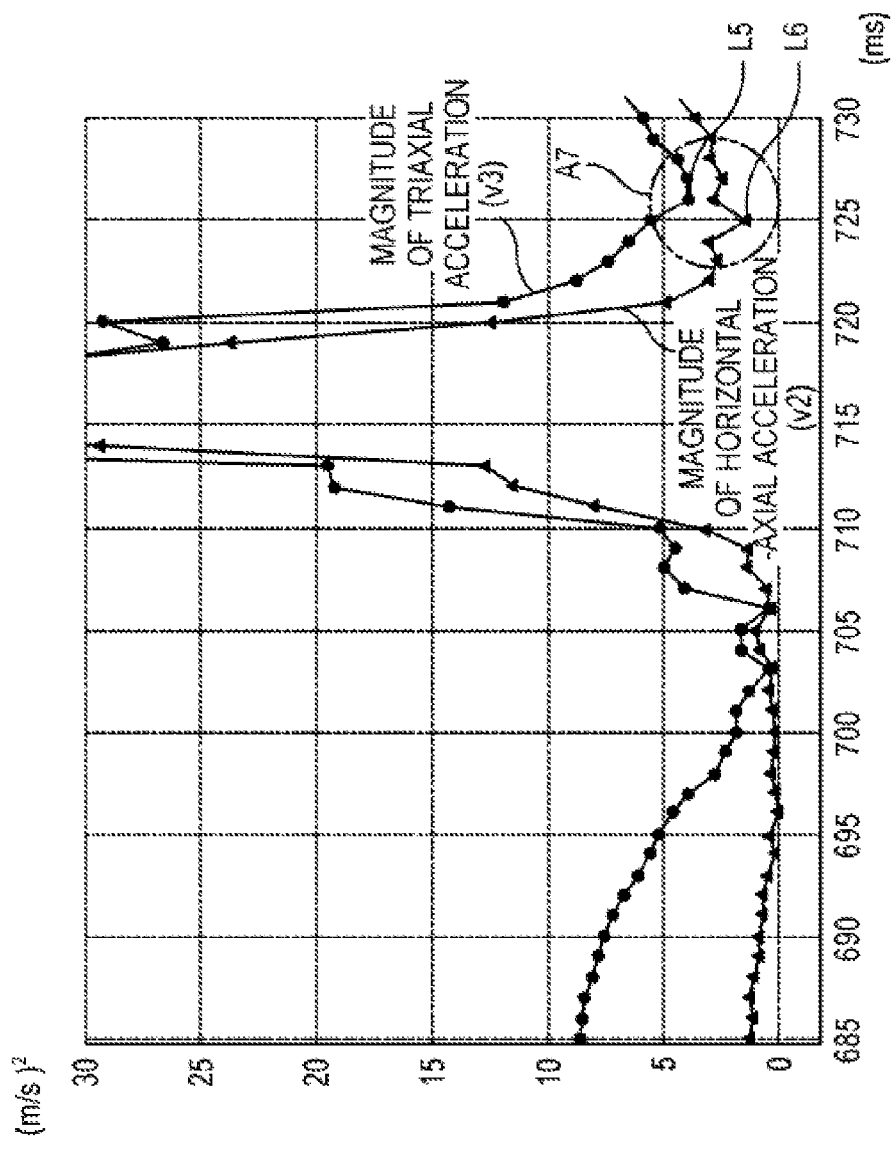

FIGS. 12 and 13 are graphs of showing magnitudes of triaxial acceleration and horizontal-axis acceleration when a human falls down backward and when a mannequin falls down backward, respectively. Referring to FIG. 12 and FIG. 13, when the human falls backward, the first lowest value L6 of the magnitude v2 of the horizontal-axis acceleration after the highest value of the magnitude v3 of the triaxial acceleration is lower than the first lowest value L5 of the magnitude v3 of the triaxial acceleration. When the mannequin falls backward, the first lowest value L8 of the magnitude v2 of the horizontal-axis acceleration after the peak value of the magnitude v3 of the triaxial acceleration is lower than the first lowest value L7 of the magnitude v3 of the triaxial acceleration. Therefore, instead of the first lowest value of the magnitude v3 of the triaxial acceleration, the first lowest value of the magnitude v2 of the horizontal-axis acceleration after the highest value of the magnitude v3 of the triaxial acceleration is used as a reference for determining a fall, and it is thus possible to lower the first lower limit used for determining the fall, thereby decreasing an error rate in recognizing the fall.

Referring back to FIG. 10 and FIG. 11, the impact caused by the backward fall of the user 30 makes the magnitude v3 of the triaxial acceleration and the magnitude v2 of the horizontal-axis acceleration increase toward the highest values H1 and H2, in which a difference Δa1 in the magnitudes v3 and v2 of the accelerations between arbitrary two points in the area where the magnitudes v3 and v2 of the accelerations are increased by the impact is greater than a difference Δa2 in the magnitudes v3 and v2 of the accelerations between arbitrary two points in the area where the magnitudes v3 and v2 of the accelerations are increased when the user 30 lies backward in FIG. 11. Therefore, when the magnitudes v3 and v2 of the acceleration are increased toward the highest values H1 and H2 by the impact, it is possible to determine a fall based on whether the difference in the magnitudes V3 and V2 of the accelerations between arbitrary two points is greater than a predetermined value within the increasing area.

Further, it is possible to determine a fall of the user 30 based on whether time Δt1 taken from the highest value H1 of the magnitude v3 of the triaxial acceleration to the first lowest value L2 of the magnitude v2 of the horizontal-axis acceleration is within a first time interval. This is because the taken time Δt1 is shorter than time Δt2 taken from the highest value H3 of the magnitude v3 of the triaxial acceleration to the first lowest value L4 of the magnitude v2 of the horizontal-axis acceleration when the user 30 lies backward.

Further, strength of a small vibration s1 after the highest value H1 in case of the fall, strength of a small vibration S3 after the highest value H3 in case of the lying, a lasting time of the small vibration, or whether a frequency of the small vibration exceeds a predetermined value may be taken into account to determine whether the user 30 falls or not. For example, when the user 30 who is in the fallen state S430 of FIG. 4 rolls on a slope along the X-Z plane with respect to the Y-axis, the acceleration in the X-axial direction and the acceleration in the Z-axial direction may show the highest value and the lowest value of the acceleration of gravity on the same cycle as the rolling cycle of the user 30. Thus, when it is detected that the magnitude of the acceleration of the motion component on the X-Z plane, i.e. the horizontal-axis acceleration has a cyclic pattern more than a predetermined upper limit, the fall detection device 300 may determine that the user 30 is rolling or rolling after falling down.

Alternatively, when the user 30 attached with the fall detection device 300 falls from a high place with intermittent collisions, free fall may be intermittently detected. Therefore, the fall detection device 300 may determine that the user 30 falls down when the acceleration in the head-axial direction, i.e. the Y-axial direction converges to 0 or is maintained within a specific range due to free fall for a predetermined period of time. Further, when the head of the user 30 faces downward, the acceleration in the Y-axial direction has a negative value and it is thus determined as a fall. When the user 30 rotates with intermittent collisions, variation in sign of acceleration may be sensed due to centrifugal force, and it is thus possible to determine whether the user 30 falls or not.

In case of frequent car accidents, the user 30 may be hit by a car and floating in the air in a going direction of the car and falls down on the ground. In this case, the fall detection device 300 senses a primary impact caused when the user 30 collides with the car, senses acceleration greater than the acceleration of gravity in a direction opposed to the acceleration of gravity when the user 30 is floating in the air, and senses an acceleration of 0 while the user 30 free-falls to the ground. The fall detection device 300 senses a secondary impact when the user 30 finally collides with the ground, thereby determining that the user 30 falls down because of the car accident.

In another case of the car accidents, the user 30 hit by the car may roll on a bonnet of the car, the fall detection device 300 senses a primary impact generated when the user 30 collides with the car, and senses that the magnitude of the horizontal-axis acceleration has a cyclic pattern more than a predetermined upper limit on the same cycle as the rolling cycle of the user 30. The fall detection device 300 senses a secondary impact when the user 30 finally collides with the ground, and thus determines that the user 30 falls down by the car accident. In this case, the fall detection device 300 determines not only whether the user 30 falls or not, but also the kind and degree of fall, thereby taking rescue activities optimized for the user 30.

Further, the fall detection device 300 compares the axial directions with respect to the highest value of the acceleration, thereby determining a falling direction of the user 30. For example, when the user 30 of FIG. 4 falls forward, the highest value of the acceleration in the Z-axial direction caused by the impact is a negative value, and thus the peak value thereof is sensed as greater than the highest value of the acceleration in the X-axial direction. On the other hand, when the user 30 falls leftward, the highest value of the acceleration in the X-axial direction caused by the impact is a negative value and sensed as greater than the peak value of the acceleration in the Z-axial direction. Thus, the fall detection device 300 determines the falling direction of the user based on comparison in sign change of acceleration between the axial directions and the highest value of acceleration between the axial directions.

FIGS. 14 to 16 are flowcharts of determining a fall. First, referring to FIGS. 14 and 15, the fall detection device 300 determines that impact occurs to the user 30 when it is sensed that at least one highest value of the accelerations in the respective axial directions is equal to or greater than the first upper limit (S1410). However, to determine whether the impact is usual or caused by a fall, it may be determined that the magnitude of the triaxial acceleration of the user 30 is maintained as 0 for a predetermined period of time before the impact (S1420). This is because the magnitude of the triaxial acceleration converges to 0 when the user 30 free-falls.

When the triaxial acceleration is maintained to have a magnitude of 0 for a predetermined period of time before the impact, the fall detection device 300 determines that the user 30 falls down, and transmits a fall fact to the external device 360(B). On the other hand, when the triaxial acceleration is not maintained to have a magnitude of 0 for the predetermined period of time before the impact, the fall detection device 300 determines whether the acceleration in the head-axial direction, i.e. the Y-axial direction is changed from a positive value to a negative value and whether the acceleration in the X-axial direction converges to 0 before the impact (S1430).

When the acceleration in the head-axial direction, i.e. the Y-axial direction is changed from a positive value to a negative value and the acceleration in the X-axial direction converges to 0 before the impact, the fall detection device 300 determines that the user 30 falls down and transmits the fall fact to the external device 360(B). On the other hand, when the acceleration in the head-axial direction, i.e. the Y-axial direction is not changed from a positive value to a negative value and the acceleration in the X-axial direction does not converge to 0 before the impact, the fall detection device 300 determines whether the highest value of the magnitude of the measured triaxial acceleration is lower than the second upper limit and equal to or higher than the first upper limit (S1440).

When the highest value of the magnitude of the triaxial acceleration is lower than the first upper limit, the fall detection device 300 determines that the user 30 does not fall down. On the other hand, when the highest value of the magnitude of the triaxial acceleration is higher than the second upper limit, the fall detection device 300 determines that the user 30 falls down and transmits the fall fact to the external device 360. However, when the highest value of the magnitude of the triaxial acceleration is between the second upper limit and the first upper limit, it is determined whether the first lowest value of the magnitude of the horizontal-axis acceleration immediately after the highest value of the magnitude of the triaxial acceleration is lower than the first lower limit and time Δt1 taken from the highest value of the magnitude of the triaxial acceleration to the lowest value of the magnitude of the horizontal-axis acceleration is within the first time interval (S1450).

When the first lowest value of the magnitude of the horizontal-axis acceleration immediately after the highest value of the magnitude of the triaxial acceleration is lower than the first lower limit and time Δt1 taken from the highest value of the magnitude of the triaxial acceleration to the lowest value of the magnitude of the horizontal-axis acceleration is within the first time interval, the fall detection device 300 determines that the user 30 falls down. Otherwise, it is finally determined whether the user 30 falls down, by determining whether a difference Δa1 in the magnitudes of the accelerations between arbitrary two points in the area where the magnitudes of the triaxial acceleration and the horizontal—axial acceleration are increasing up to the maximum value is within a predetermined range, whether an amplitude of the small vibration is equal to or higher than a predetermined value after the peak value of the magnitude of the triaxial acceleration, and whether a frequency of the small vibration is equal to or higher than a predetermined value (S1460).

Referring to FIG. 16, a fall determination method of FIG. 16 primarily determines whether the user 30 falls down or not through the method shown in FIGS. 14 and 15, and then secondarily determines whether the user 30 falls down or not, thereby decreasing an error rate in recognizing a fall and minimizing wasteful notice of the fall. The fall detection device 300 primarily determines whether the user 30 falls down or not through the fall determination method shown in FIGS. 14 and 15 (S1610). However, even when the user 30 recovers his/her consciousness and gets up after his/her fall is primarily detected, it may be still determined that the user 30 falls down. Accordingly, it is secondarily taken into account for the fall determination whether the user 30 who lost his/her consciousness and fell down cannot get up and is still lying, thereby lowering an error rate in recognizing the fall.

To this end, the error rate in recognizing the fall is lowered by considering an acceleration component of each axis. Specifically, when the acceleration in the head-axial direction, i.e. the Y-axial direction is lower than a third upper limit and the magnitude of the horizontal-axis acceleration, i.e. the magnitudes of the acceleration in the X-axial direction and the acceleration in the Z-axial direction are greater than the second lower limit after the primary fall detection, it may be determined that the user is still lying after the fall detection (S1620). In this case, when a motion index of indicating that the user 30 has no motions or a little motion is lower than a fourth upper limit while the user 30 is lying, it may be determined that the user 30 is in a serious condition after the fall. Here, the motion index may be determined as the highest value of the triaxial acceleration, an average magnitude of the triaxial acceleration or a standard deviation in the magnitude of the triaxial acceleration. When the motion index is within a predetermined lower limit, it may be determined that the motion index is small. Further, when a proportion of time, during which the motion index is higher than a predetermined upper limit, of a predetermined time interval after the fall detection, it may be determined that the motion index is small.

When the time during which the user 30 is lying after the fall is greater than a third lower limit, it is determined that the user 30 cannot inform others of his/her fall by him/herself, and thus the fall detection device 300 notifies others of the final fall determination of the user (S1630). Thus, it is possible to lower the error rate in recognizing the fall since the secondary fall determination is used after the primary fall determination.

Figure 17:
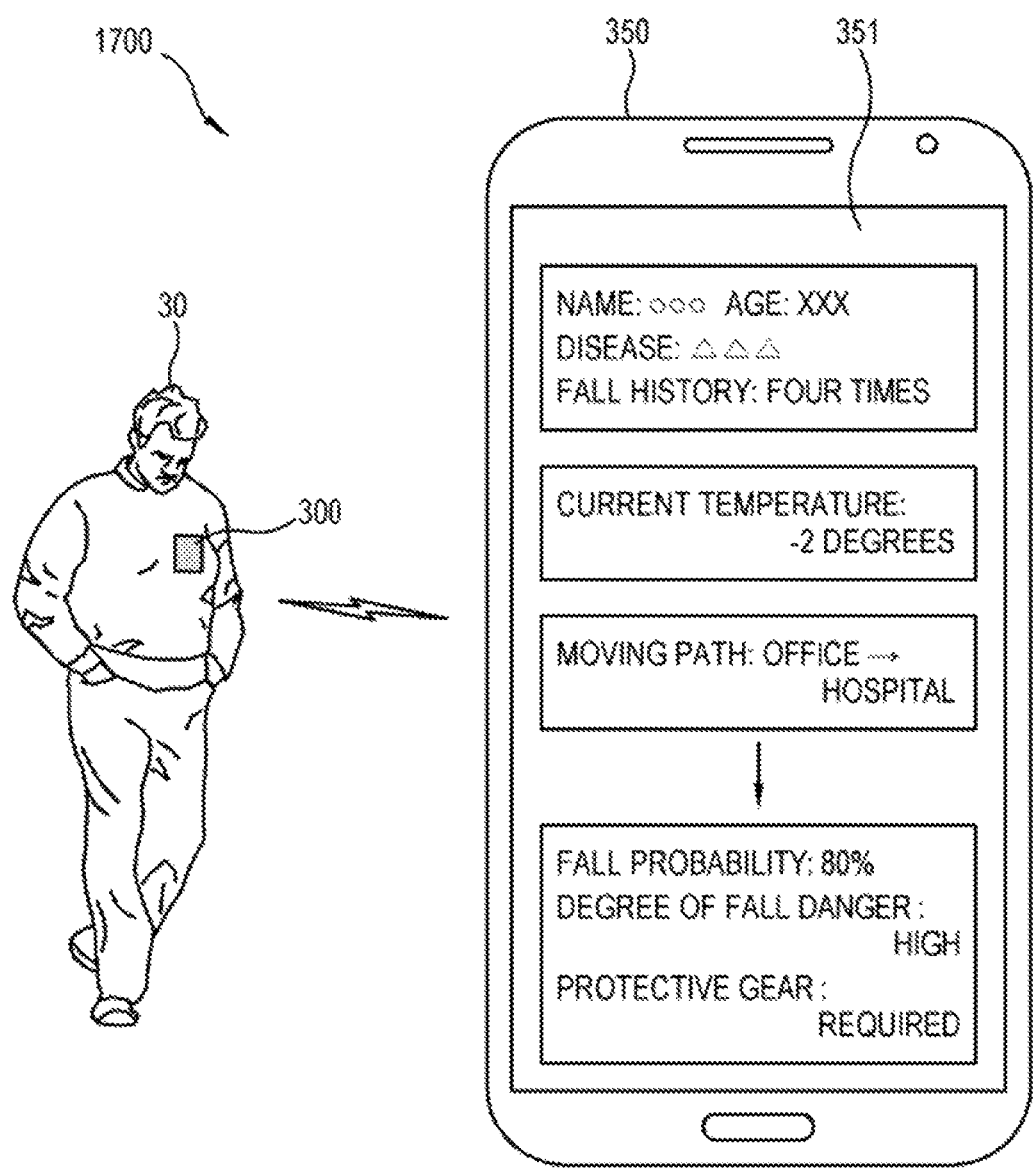
FIG. 17 illustrates an example of the fall detection system including the fall detection device of FIG. 3.

FIG. 17 illustrates an example of the fall detection system including the fall detection device of FIG. 3. Referring to FIG. 17, a fall detection system 1700 may include the fall detection device 300 and an external device 350. The external device 350 may include a smart phone with a display 351, and a display apparatus.

The external device 350 may provide fall prevention information to the user 30 who wears the fall detection device 300. For example, the external device 350 may receive user information about the user 30 from the communicator 340 of the fall detection device 300. The user information may include personal information, body information, and fall-related information of the user 30. The external device 350 shows the user a fall probability and a degree of fall danger through the display 351 by taking the user information and environmental information including the current weather into account, and displays an image of recommending a fall preventing clothes or shoes on the display 351.

In addition, the external device 350 may make the display 351 display a user interface (UI) or a graphic user interface (GUI) for voluntarily adjusting the user information and the environmental information. For example, the external device 350 may make the display 351 display the UI for allowing the user 30 to input his/her moving path. When the user 30 inputs a path, via which s/he will move, through the UI, the external device 350 displays a fall probability and a degree of fall danger on the moving path by taking the user information and the environmental information into account.

The foregoing embodiments are only illustrative purposes, and it will be appreciated by a person having an ordinary skill in the art that various changes and other equivalent embodiments can be made. Therefore, the scope of the present invention is defined in the appended claims.

The invention claimed is:

1. A fall detection device comprising:
   at least one sensor which is attached to a user and senses a motion of the fall detection device in a plurality of coordinate axial directions comprising a first axial direction and a second axial direction perpendicular to the first axial direction;
   an output section which outputs fall information of the user; and
   a processor which:
      determines that the user falls down based on obtaining that acceleration in the first axial direction is changed from a positive value to a negative value, and acceleration in the second axial direction is lower than a first lower limit before impact occurs to the user while the acceleration in the first axial direction is changed from the positive value to the negative value based on the sensed motion of the fall detection device, and
      controls the output section to output the fall information that the user falls down.

2. The fall detection device according to claim 1, wherein the first axial direction is perpendicular to a ground.

3. The fall detection device according to claim 1, wherein the processor determines that the impact occurs to the user before acceleration of motion components on first axis-second axis-third axis among a plurality of coordinate axes equals to a first upper limit based on the acceleration of motion components on the first axis-second axis-third axis being higher than the first upper limit.

4. The fall detection device according to claim 3, wherein the processor determines that the user falls down based on obtaining that acceleration of a motion component on a second axis-third axis plane is lower than or equal to a second lower limit after the impact occurs, in the case where the acceleration in the first axial direction is changed from the positive value to the negative value.

5. The fall detection device according to claim 4, wherein it is determined that the user falls down based on obtaining that time elapsed until the acceleration of the motion component on the second axis-third axis plane reaches the second lower limit after the impact occurs is within a first threshold.

6. The fall detection device according to claim 1, wherein the output section comprises a communicator for transmitting the fall information to an external device.

7. A method for a fall detection device, comprising:
   sensing, by at least one sensor, a motion of the fall detection device in a plurality of coordinate axial directions comprising a first axial direction and a second axial direction perpendicular to the first axial direction while the fall detection device is attached to a user;
   determining, by a processor, that the user falls down based on obtaining that acceleration in the first axial direction is changed from a positive value to a negative value, and acceleration in the second axial direction is lower than a first lower limit before impact occurs to the user while the acceleration in the first axial direction is changed from the positive value to the negative value based on the sensed motion of the fall detection device; and
   outputting, by an output section, fall information that the user falls down.

8. The method according to claim 7, wherein the first axial direction is perpendicular to a ground.

9. The method according to claim 7, wherein the determining that the user falls down comprises determining that the impact occurs to the user before acceleration of motion components on first axis-second axis-third axis among a plurality of coordinate axes equals to a first upper limit based on the acceleration of motion components on the first axis-second axis-third axis being higher than the first upper limit.

10. The method according to claim 9, wherein the determining that the user falls down comprises determining that the user falls down based on obtaining that acceleration of a motion component on a second axis-third axis plane is lower than or equal to a second lower limit after the impact occurs, in the case where the acceleration in the first axial direction is changed from the positive value to the negative value.

11. The method according to claim 10, wherein the determining that the user falls down comprises determining that the user falls down based on obtaining that time elapsed until the acceleration of the motion component on the second axis-third axis plane reaches the second lower limit after the impact occurs is within a first threshold.

12. The method according to claim 7, further comprising transmitting the fall information to an external device.

* * * * *